US009101365B2

(12) United States Patent
Highsmith

(10) Patent No.: US 9,101,365 B2
(45) Date of Patent: Aug. 11, 2015

(54) CATHETER WITH MULTIPLE ELECTRODE ASSEMBLIES FOR USE NEAR TUBULAR REGIONS OF THE HEART

(71) Applicant: BIOSENSE WEBSTER, INC., Diamond Bar, CA (US)

(72) Inventor: Debby Esther Highsmith, Laguna Niguel, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 14/261,326

(22) Filed: Apr. 24, 2014

(65) Prior Publication Data
US 2014/0350552 A1  Nov. 27, 2014

Related U.S. Application Data

(63) Continuation of application No. 12/346,829, filed on Dec. 30, 2008, now Pat. No. 8,712,550.

(51) Int. Cl.
A61N 1/00 (2006.01)
A61B 18/14 (2006.01)
(Continued)

(52) U.S. Cl.
CPC ... A61B 18/1492 (2013.01); *A61B 2017/00867* (2013.01); *A61B 2018/00214* (2013.01);
(Continued)

(58) Field of Classification Search
USPC ............ 600/372–373, 377, 381, 466; 606/32, 606/37–41; 607/119, 122, 124
See application file for complete search history.

(56) References Cited

U.S. PATENT DOCUMENTS

| 4,898,591 A | 2/1990 | Jang et al. |
| 5,104,393 A | 4/1992 | Isner et al. |

(Continued)

FOREIGN PATENT DOCUMENTS

| JP | 2001-504363 A | 4/2001 |
| JP | 2003-514612 A | 4/2003 |

(Continued)

OTHER PUBLICATIONS

European Patent Office Extended European Search Report for European Patent No. 11155246.9, dated Nov. 29, 2011. 14 pgs.
(Continued)

*Primary Examiner* — Joseph Stoklosa
*Assistant Examiner* — Brian M Antiskay
(74) *Attorney, Agent, or Firm* — Christie, Parker & Hale, LLP

(57) ABSTRACT

A catheter with ablation and potential sensing capabilities is adapted for outer circumferential contact with an opening of a tubular region and inner circumferential contact within the tubular region. The catheter has a proximal electrode assembly and a distal electrode assembly for ablation of an ostium and potential sensing inside the pulmonary vein so that it is possible to obtain ECG signals inside a pulmonary vein when ablating around the ostium. The distal electrode assembly has an elongated member defining a longitudinal axis and a plurality of spines surrounding the member and converging at their proximal and distal ends, where each spine has at least one electrode and a curvature so that the spine bows radially outwardly from the member. The proximal electrode assembly has a proximal electrode assembly has an elongated member configured with a generally radial portion and a generally circular portion generally transverse to the catheter axis, where the generally circular portion comprising a plurality of electrodes. The control handle advantageously allows a user to manipulate a tensile member for changing the curvature of the spine.

17 Claims, 15 Drawing Sheets

(51) Int. Cl.
  *A61B 5/04* (2006.01)
  *A61B 8/14* (2006.01)
  *A61B 17/00* (2006.01)
  *A61B 18/00* (2006.01)

(52) U.S. Cl.
  CPC .............. *A61B2018/00351* (2013.01); *A61B 2018/00375* (2013.01); *A61B 2018/00577* (2013.01); *A61B 2018/00839* (2013.01); *A61B 2018/141* (2013.01); *A61B 2018/1407* (2013.01); *A61B 2018/1465* (2013.01); *A61B 2018/1467* (2013.01); *A61B 2018/1475* (2013.01); *C08L 2201/12* (2013.01)

(56) References Cited

U.S. PATENT DOCUMENTS

| | | | |
|---|---|---|---|
| 5,487,385 | A | 1/1996 | Avitall |
| 5,575,766 | A | 11/1996 | Swartz et al. |
| 5,582,609 | A | 12/1996 | Swanson et al. |
| 5,617,854 | A | 4/1997 | Munsif |
| 5,752,518 | A | 5/1998 | McGee et al. |
| 5,938,660 | A | 8/1999 | Swartz et al. |
| 5,964,757 | A | 10/1999 | Ponzi |
| 5,971,983 | A | 10/1999 | Lesh |
| 6,004,269 | A | 12/1999 | Crowley et al. |
| 6,012,457 | A | 1/2000 | Lesh |
| 6,014,579 | A | 1/2000 | Pomeranz et al. |
| 6,024,740 | A | 2/2000 | Lesh et al. |
| 6,064,902 | A | 5/2000 | Haissaguerre et al. |
| 6,090,084 | A | 7/2000 | Hassett et al. |
| 6,117,101 | A | 9/2000 | Diederich et al. |
| 6,164,283 | A | 12/2000 | Lesh |
| 6,245,064 | B1 | 6/2001 | Lesh et al. |
| 6,251,109 | B1 | 6/2001 | Hassett et al. |
| 6,500,167 | B1 | 12/2002 | Webster, Jr. |
| 6,522,933 | B2 | 2/2003 | Nguyen |
| 6,529,756 | B1 | 3/2003 | Phan et al. |
| 6,607,520 | B2 | 8/2003 | Keane |
| 6,669,693 | B2 | 12/2003 | Friedman |
| 6,728,455 | B2 | 4/2004 | Kusakari et al. |
| 6,741,878 | B2 | 5/2004 | Fuimaono et al. |
| 6,745,080 | B2 | 6/2004 | Koblish |
| 6,771,996 | B2 | 8/2004 | Bowe et al. |
| 6,972,016 | B2 | 12/2005 | Hill, III et al. |
| 6,973,339 | B2 | 12/2005 | Govari |
| 6,987,995 | B2 | 1/2006 | Drysen |
| 7,003,342 | B2 | 2/2006 | Plaza |
| 7,142,903 | B2 | 11/2006 | Rodriguez et al. |
| 7,285,119 | B2 | 10/2007 | Stewart et al. |
| 7,285,120 | B2 | 10/2007 | Im et al. |
| 7,306,594 | B2 | 12/2007 | Collins et al. |
| 7,412,273 | B2 | 8/2008 | Jais et al. |
| 2002/0177765 | A1 | 11/2002 | Bowe et al. |
| 2003/0114739 | A1 | 6/2003 | Fuimaono et al. |
| 2004/0181135 | A1 | 9/2004 | Drysen |
| 2005/0010095 | A1 | 1/2005 | Stewart et al. |
| 2005/0187546 | A1 | 8/2005 | Bek et al. |
| 2007/0129721 | A1 | 6/2007 | Phan et al. |
| 2007/0270794 | A1 | 11/2007 | Anderson et al. |
| 2009/0253976 | A1 | 10/2009 | Harlev et al. |

FOREIGN PATENT DOCUMENTS

| | | |
|---|---|---|
| JP | 2003-522561 A | 7/2003 |
| WO | WO 93/20767 | 10/1993 |
| WO | WO 01/37925 A2 | 5/2001 |
| WO | WO 02/089687 A1 | 11/2002 |
| WO | WO 02/094115 A2 | 11/2002 |

OTHER PUBLICATIONS

English translation of SIPO Search Report dated Mar. 26, 2013 in CN application No. 200910263743.7 (2 pages).
JP Office action dated Oct. 8, 2013, issued to JP application No. 2009-297011 (2 pages).

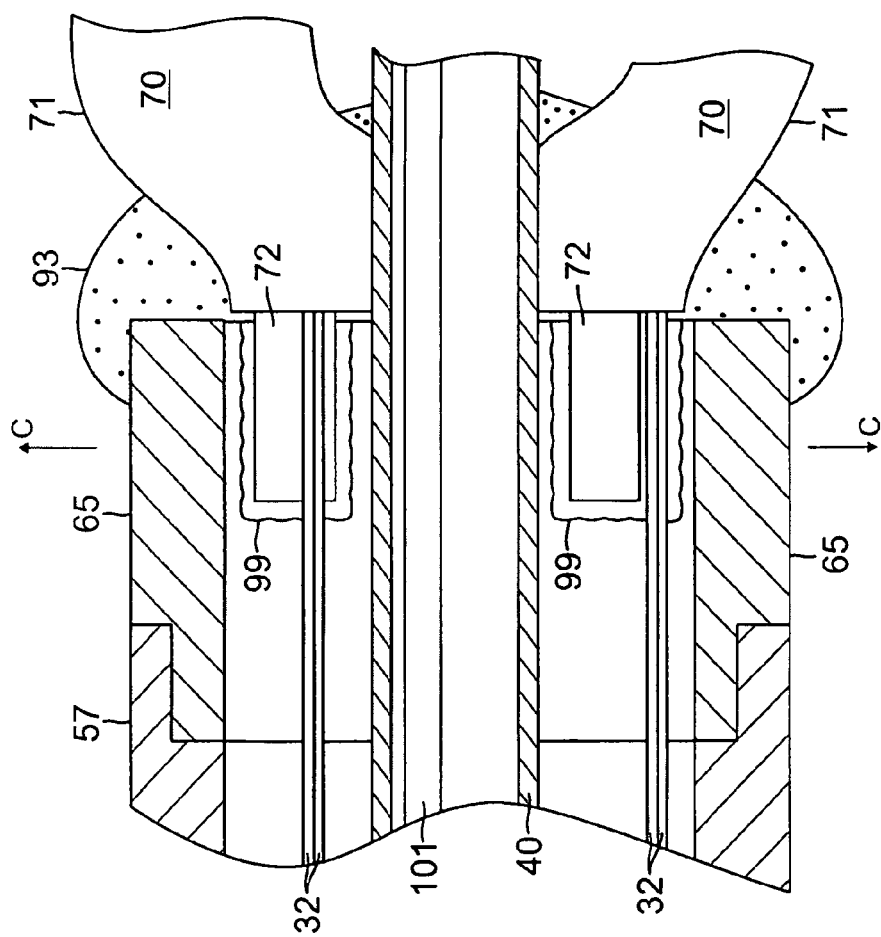
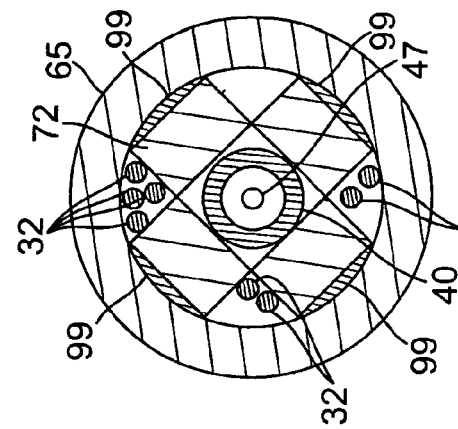

CATHETER WITH MULTIPLE ELECTRODE ASSEMBLIES FOR USE NEAR TUBULAR REGIONS OF THE HEART

CROSS-REFERENCE TO RELATED APPLICATION

This application is a continuation of U.S. patent application Ser. No. 12/346,829, filed Dec. 30, 2008, the entire content of which is incorporated herein by reference.

FIELD OF INVENTION

This present invention relates to an improved electrophysiologic catheter that is particularly useful for ablation and sensing electrical activity at or near a tubular region of the heart.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reenetrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

It has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions.

Examples of catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang, et al., U.S. Pat. No. 5,487,385 to Avitall, and U.S. Pat. No. 5,582,609 to Swanson, the disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in WO 93/20767 to Stem, et al., U.S. Pat. No. 5,104,393 to Isner, et al. and U.S. Pat. No. 5,575,766 to Swartz, et al., respectively, the entire disclosures of which are incorporated herein by reference.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

Mapping and ablation in regions of or near the pulmonary veins poses special challenges due to the configuration of the ostia and surrounding tubular tissue. Catheters have been developed that are particularly useful for mapping and ablating the pulmonary veins and other tubular regions of or near the heart, including the ostium. U.S. Pat. Nos. 6,090,084 and 6,251,109 to Hassett et al., U.S. Pat. No. 6,117,101 to Diederich et al., U.S. Pat. No. 5,938,660 to Swartz et al., U.S. Pat. Nos. 6,245,064 and 6,024,740 to Lesh et al., U.S. Pat. Nos. 5,971,983, 6,012,457 and 6,164,283 to Lesh, U.S. Pat. No. 6,004,269 to Crowley et al., and U.S. Pat. No. 6,064,902 to Haissaguerre et al., all of which are incorporated herein by reference, describe apparatus for tissue ablation to treat atrial arrhythmia, primarily tissue located within the pulmonary veins or on the ostia of the pulmonary veins. Catheters having lasso, open-spine or closed-spine (basket) assemblies are also known. Such catheters are disclosed in, for example, U.S. Pat. Nos. 6,728,455, 6,973,339, 7,003,342, 7,142,903, and 7,412,273, the entire disclosures of which are hereby incorporated by reference.

"Lasso" catheters are particularly useful during circumferential ablations around the ostium of the pulmonary veins. One technique utilizes one catheter for mapping and finding abnormal potentials and a second catheter for ablating the ostium. However, during a procedure it is desirable to have continuous feedback of the potential recordings or electrograms (ECGs) inside the pulmonary vein (PV) as a circumferential ablation is performed around the vein's ostium. Having feedback of the ECGs inside a pulmonary vein during PV ostium ablation allows a user to know whether the undesired potentials have been successfully blocked by the circumferential ablation. Currently, if the user desires real time ECG feedback from inside the pulmonary vein during a circumferential ablation, a third catheter is used. Accordingly, it is desired that a single catheter be adapted to both ablate and detect potentials, and in particular, that a single catheter have both a proximal electrode assembly for ablating an ostium and a distal electrode assembly for detecting potentials in the tubular region of the ablated ostium so that it is possible to obtain ECG signals inside a pulmonary vein when ablating around the ostium.

SUMMARY OF THE INVENTION

The present invention is directed to a catheter with ablation and potential sensing capabilities that is adapted for outer circumferential contact with an opening of a tubular region and inner circumferential contact within the tubular region. In one embodiment, the present invention provides a single catheter having both a proximal electrode assembly and a distal electrode assembly for ablation of an ostium and potential sensing inside the pulmonary vein so that it is possible to obtain ECG signals inside a pulmonary vein when ablating around the ostium.

In a more detailed embodiment, the catheter has an elongated catheter body and a control handle at its proximal end. At its distal end is an electrode structure comprising a distal electrode assembly and a proximal electrode assembly. The distal electrode assembly has an elongated member defining a longitudinal axis and a plurality of spines surrounding the member and converging at their proximal and distal ends, where each spine has at least one electrode and a curvature so that the spine bows radially outwardly from the member. The proximal electrode assembly has a proximal electrode assembly has an elongated member configured with a generally radial portion and a generally circular portion generally transverse to the catheter axis, where the generally circular portion comprising a plurality of electrodes. The control handle advantageously allows a user to manipulate a tensile member for changing the curvature of the spine. The catheter may also have a deflectable section between the catheter body and the electrode structure where the control handle allows a user to manipulate a second tensile member for deflecting the deflectable section.

In a more detailed embodiment, the catheter may have electrodes on the distal electrode assembly that are adapted for sensing electrical activity in the heart while having electrodes on the proximal electrode assembly that are adapted for ablation. Moreover, the electrode assemblies may have shape-memory elements to help the assemblies retain their shape.

In another embodiment, the catheter has a control handle has control members that allow separate and independent control of tensile members to deflect the intermediate section, to expand a basket electrode assembly, and/or to contract a lasso electrode assembly. In a detailed embodiment, the control handle has a thumb control and a rotatable grip to draw different puller, deflection or contraction wires.

In a more detailed embodiment, the control handle has a handle body, a core and a piston that is longitudinally moveable relative to the core and handle body. There are also a first anchor fixedly mounted to the core, a cam receiver mounted within the handle body, a second anchor fixedly mounted to the cam receiver, and a cylindrical cam mounted distal to the cam receiver in surrounding relation to the piston, wherein rotation of the cam relative to the piston causes longitudinal movement of the cam receiver and second anchor.

BRIEF DESCRIPTION OF THE DRAWINGS

These and other features and advantages of the present invention will be better understood by reference to the following detailed description when considered in conjunction with the accompanying drawings wherein:

FIG. 7b is a side cross sectional view of an embodiment of a catheter of the present invention, including a proximal end of a distal electrode assembly, taken along another diameter.

FIG. 7c is an end cross-sectional view of a proximal end of a distal electrode assembly of FIGS. 7a and 7b taken along line c-c.

DETAILED DESCRIPTION OF THE INVENTION

Figure 1A:
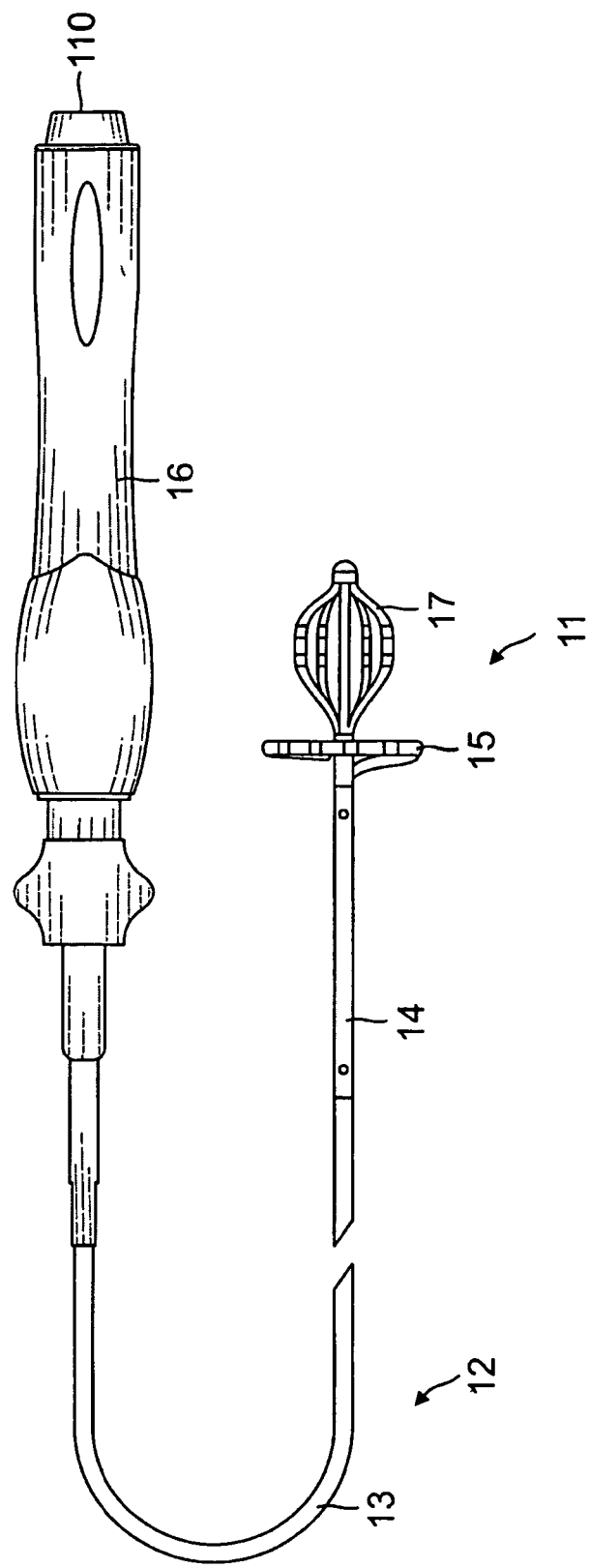
FIG. 1a is a top view of an embodiment of the catheter of the present invention.
Figure 1B:
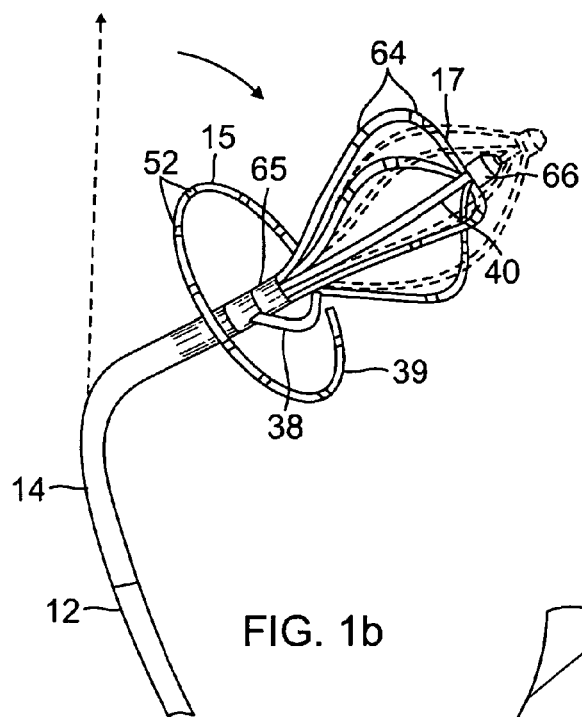
FIG. 1b is a perspective view of an embodiment of an electrode structure of the present invention, including a proximal electrode assembly and a distal electrode assembly, wherein the distal electrode assembly is shown in a normal configuration (broken lines) and in an expanded configuration (solid lines).

In a disclosed embodiment of the invention, there is provided a catheter 10 having an electrode structure 11 at its distal end. As shown in FIGS. 1a and 1b, the catheter comprises an elongated catheter body 12 having proximal and distal ends, an intermediate deflectable section 14 at the distal end of the catheter body, and a control handle 16 at the proximal end of the catheter body. The electrode structure 11 extending from the intermediate section 14 has a proximal electrode assembly 15 and a distal electrode assembly 17. In the illustrated embodiment with reference to FIG. 2, the proximal electrode assembly 15 is lasso-shaped to sit on an opening 19 of a tubular region 21 of the heart, for example, an ostium of a pulmonary vein, for circumferential tissue contact at the opening. The distal electrode assembly 17 is basket-shaped to extend past the opening 19 and into the tubular region for circumferential tissue contact with an inner surface 23 of the tubular region. In that regard, the distal electrode assembly 17 is expandable to a greater diameter to ensure contact with the inner surface 23.

Figure 3A:
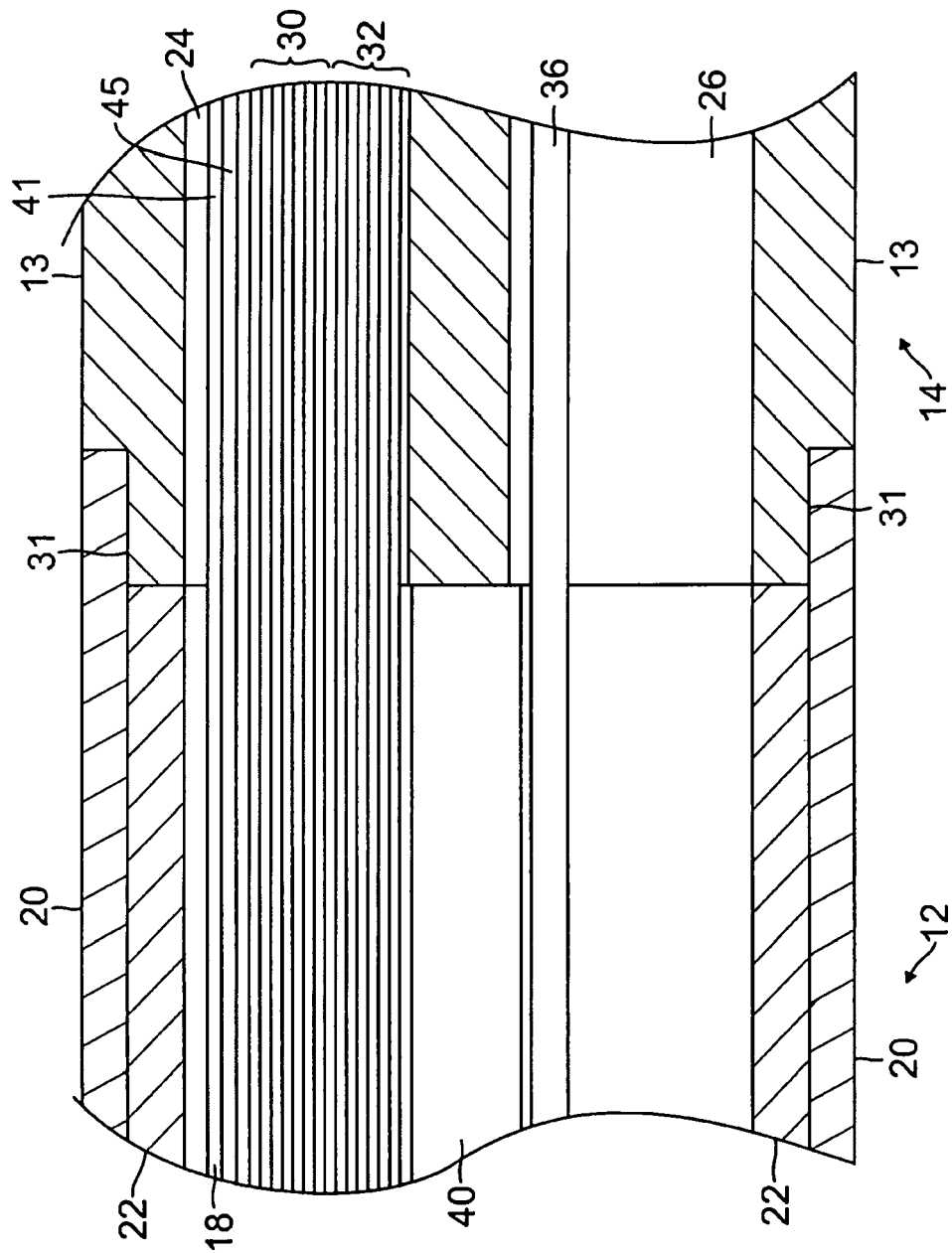
FIG. 3a is a side cross-sectional view of an embodiment of a catheter of the present invention, including a junction between a catheter body and an intermediate section along one diameter.
Figure 3B:
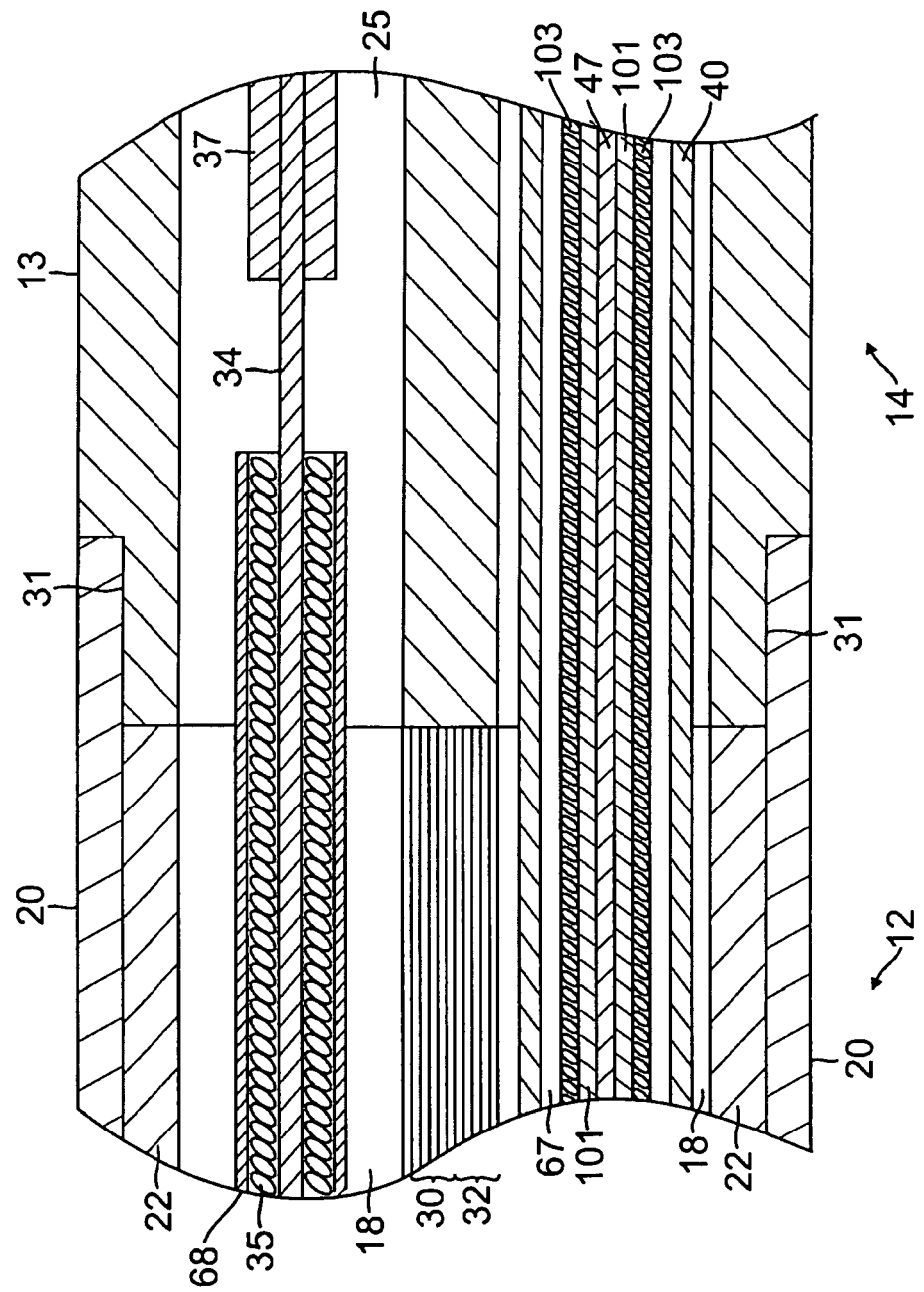
FIG. 3b is a side cross-sectional view of an embodiment of a catheter of the present invention, including a junction between a catheter body and an intermediate section along another diameter.

With reference to FIGS. 3a and 3b, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller wires, lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Figure 4:
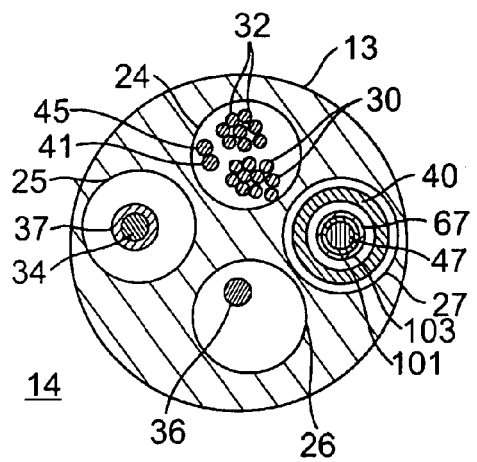
FIG. 4 is an end cross-sectional view of an embodiment of an intermediate section of the catheter of the present invention.

With additional reference to FIG. 4a, the intermediate section 14 comprises a short section of tubing 13 having multiple lumens, for example three to five lumens. In the disclosed embodiment, there are lumens 24, 25, 26 and 27. The first lumen 24 carries lead wires 30 for ring electrodes of the lasso electrode assembly 15, lead wires 32 for ring electrodes of the basket electrode assembly 17, and thermocouple wires 41 and 45 for measuring temperature, for example, at the ring electrode(s), where the catheter is constructed for bipolar ablation. The second lumen 25 carries a first tensile member or deflection wire 34 for deflecting the intermediate section 14. The third lumen 26 carries a cable 36 for an electromagnetic location sensor 33 located at or near the electrode structure 11. The fourth lumen 27 carries a tubing 40 having a lumen 67 suitable for a guidewire to pass, and through which a second tensile member or puller wire 47 extends for expanding the basket electrode assembly 17.

The tubing 13 of the intermediate section 14 is made of a suitable non-toxic material that is preferably more flexible than the catheter body 12. A suitable material for the tubing 13 is braided PEBAX or polyurethane, i.e., polyurethane with an embedded mesh of braided stainless steel or the like. The size of each lumen is not critical, but is sufficient to house the respective components extending therethrough.

The useful length of the catheter, i.e., that portion that can be inserted into the body excluding the assemblies 15 and 17, can vary as desired. In one embodiment, the useful length ranges from about 110 cm to about 120 cm. The length of the intermediate section 14 is a relatively small portion of the useful length, and preferably ranges from about 3.5 cm to about 10 cm, more preferably about 4 cm to about 8 cm, and still more preferably about 6.5 cm.

A means for attaching the catheter body 12 to the intermediate section 14 is illustrated in FIGS. 3a and 3b. The proximal end of the intermediate section 14 comprises an outer circumferential notch 31 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 2:
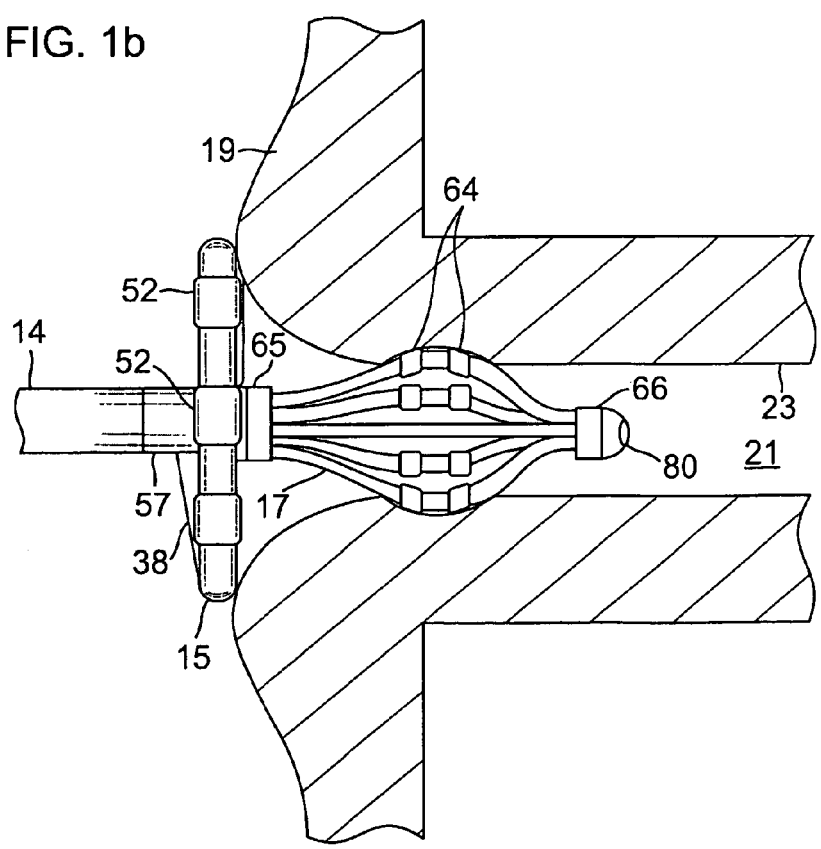
FIG. 2 is side elevational view of an embodiment of an electrode structure positioned with a distal electrode assembly positioned in a tubular region of the heart and a proximal electrode assembly on an ostium of the tubular region.
Figure 5B:
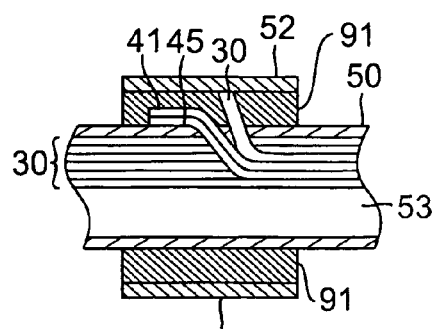
FIG. 5b is a detailed view of an alternative embodiment of a portion of an electrode structure, including a ring electrode, thermocouple wires and a lead wire.
Figure 5A:
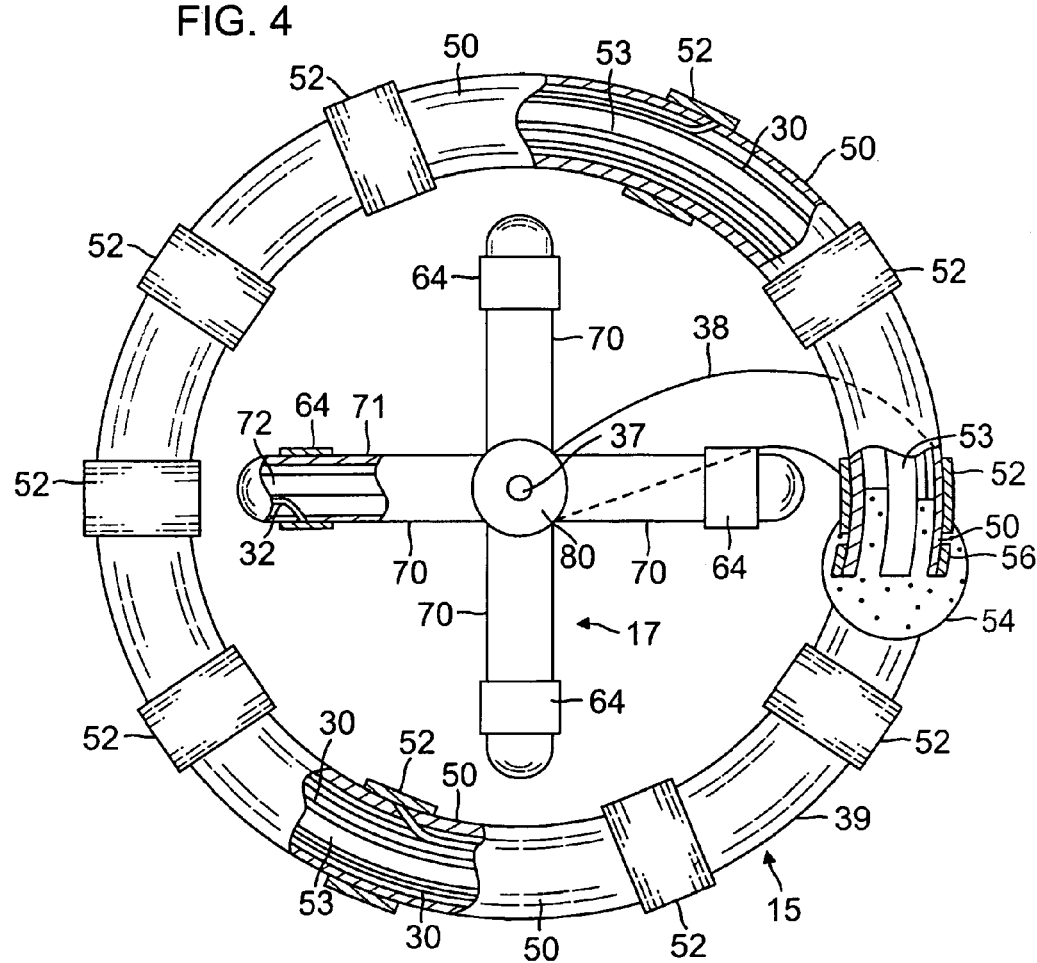
FIG. 5a is an end view of an embodiment of an electrode structure, including a proximal electrode assembly and a distal electrode assembly.

At the distal end of the intermediate section 14 is the electrode structure 11 having a proximal assembly 15 adapted to sit on an opening of a tubular region, and a distal assembly 17 adapted to enter the tubular region and contact the inner surface of the tubular region (FIG. 2). The assemblies 15 and 17 are generally concentric about the axis of the deflectable intermediate section 14. With reference to FIGS. 1b and 5a, the proximal assembly 15 comprises a connecting segment 38 and a generally circular main segment 39. The segment 38 is generally straight and extending radially from the distal end of the intermediate section 14. The length of the segment 38 is about equal to the radius of the generally circular main segment 39 such that the generally circular main segment is generally concentric with the distal end of the intermediate section 14. The proximal assembly 15 has an exposed length, e.g., not contained within the intermediate section 14, ranging between about 20 mm and about 70 mm, more preferably about 25 mm and about 50 mm, still more preferably about 42 mm, but can vary as desired.

The generally circular main segment 39 is generally traverse to the catheter body 12 and is preferably generally perpendicular to the catheter body 12. The generally circular main segment 39 need not form a flat circle, but can be very slightly helical. The main segment 39 has an exposed length ranging between about 40 mm and 100 mm, more preferably about 50 mm and 90 mm, and still more preferably about 60 mm, and an outer diameter preferably ranging to about 10 mm to about 35 mm, more preferably about 15 mm to about 30 mm, still more preferably about 25 mm. The main segment 39 can curve in a clockwise direction, as shown in FIG. 6 or a counterclockwise direction, as shown in FIG. 1b.

The proximal assembly 15 comprises a non-conductive covering or tubing 50 (shown partially broken away in FIG. 5a) that spans the length of the segments 38 and 39. The covering or tubing 50 can be made of any suitable material that is flexible and biocompatible and preferably plastic, such as polyurethane or PEBAX. The tubing 50 (as with all tubes or tubing herein) may have any cross-sectional shape and may have a single lumen or multiple lumens. The illustrated embodiment, the tubing 50 has a single lumen that is occupied by lead wires 30 or other electrical connections for ring electrodes 52 or any other electrical or electromagnetic elements that may be mounted on the proximal assembly 15. Moreover, the lumen is occupied by a support element 53 that can have shape memory or be preformed with the radial and generally circular shape. A shape memory element can be straightened or bent out of its original shape upon exertion of a force and is capable of substantially returning to its original shape upon removal of the force. A suitable material for the shape memory element is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability.

Figure 6A:
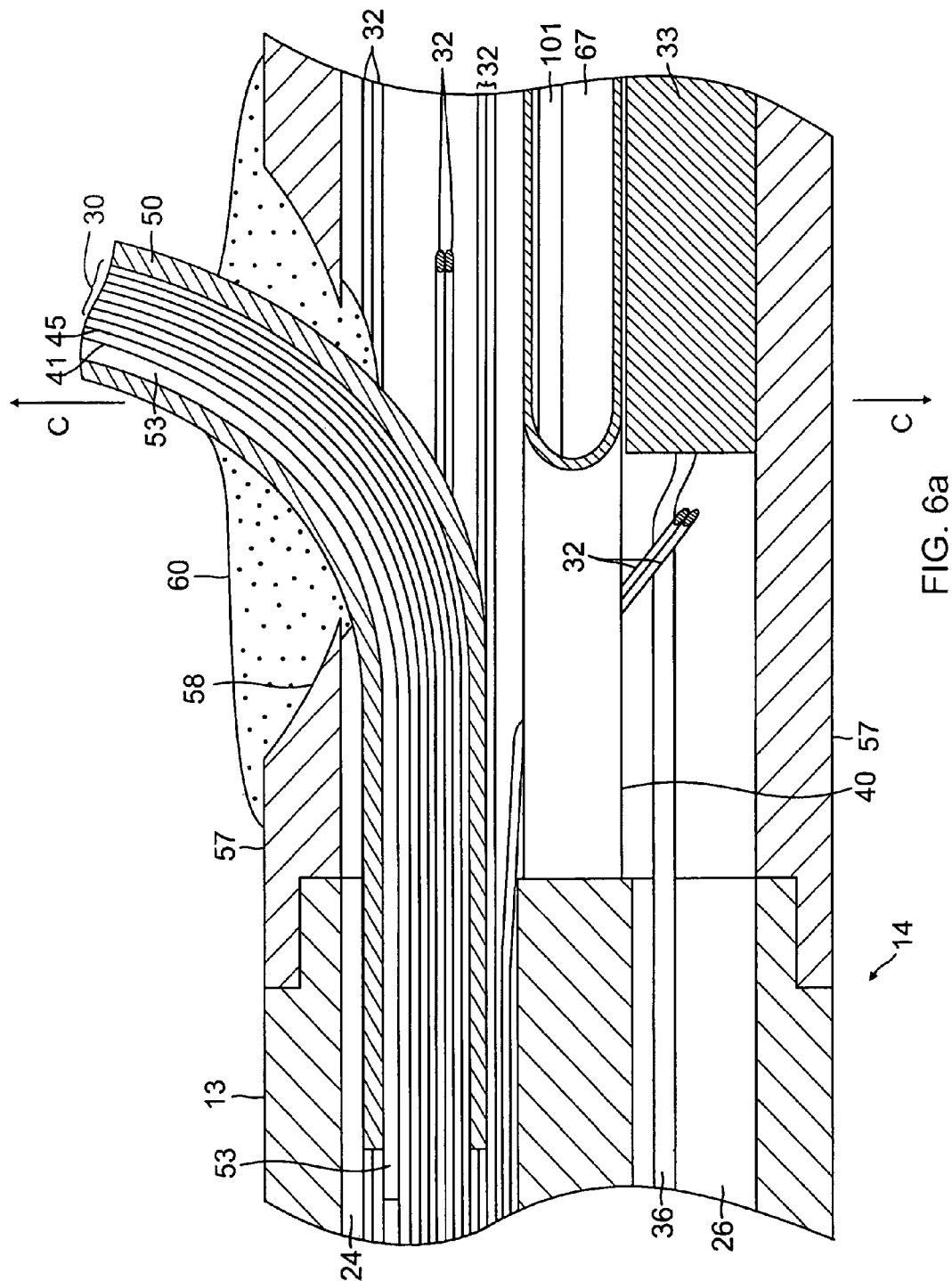
FIG. 6a is a side cross-sectional view of an embodiment of a catheter of the present invention, including a junction of an intermediate section and a connector tubing, taken along one diameter.

A means for attaching the tubing 50 of the proximal electrode assembly 15 to the catheter is illustrated in FIGS. 4*b* and 6*a*. A nonconductive connector tubing 57 constructed of a biocompatible materials, e.g., PEEK, with a single lumen, extends from the distal end of the tubing 13 of the intermediate section 14. An opening 58 is cut or otherwise formed in the wall of the tubing 57 to receive a proximal end of the tubing 50 which can extend proximally into the lumen 24 of the tubing 13 and be affixed by glue 60 which also seals the opening 58. The lead wires 30 for the proximal assembly 15 extend from the lumen 24 of the tubing 13 of the intermediate section 14, and into the tubing 50 where they pass through the radial segment 38 and the generally circular main segment 39 of the proximal assembly 15. On the generally circular main segment 39 are mounted multiple ring electrodes 52, each connected to a respective lead wire 30 as shown in FIGS. 5*a* and 5*b*. The support member 53 also extends through the length of the tubing 50 to give shape and support to the segments 38 and 39 of the proximal assembly 15. A proximal end of the member 53 is anchored in the lumen 24 of the intermediate section 14 (FIG. 6*a*).

As shown in FIG. 5*a*, the distal end of the proximal assembly 15 is sealed with a dome 54 of polyurethane glue or the like. A short ring 56, made of metal or plastic, and preferably polyamide, is mounted within the distal end of the non-conductive cover 50. The short ring 56 prevents the distal end of the non-conductive cover 50 from collapsing, there by maintaining the diameter of the non-conductive cover at its distal end.

Figure 6B:
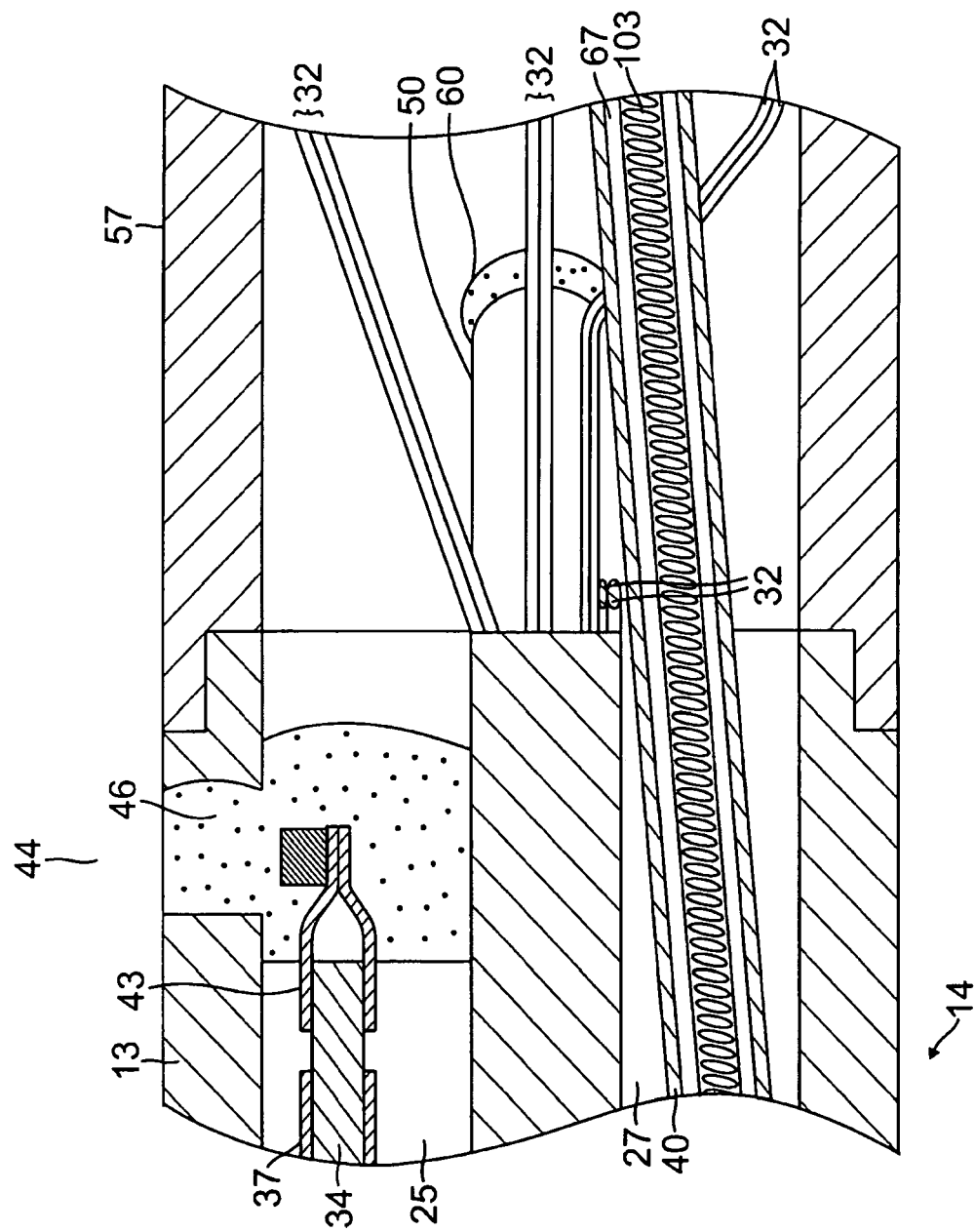
FIG. 6b is a side cross-sectional view of an embodiment of a catheter of the present invention, including a junction of an intermediate section and a connector tubing, taken along another diameter.
Figure 6C:
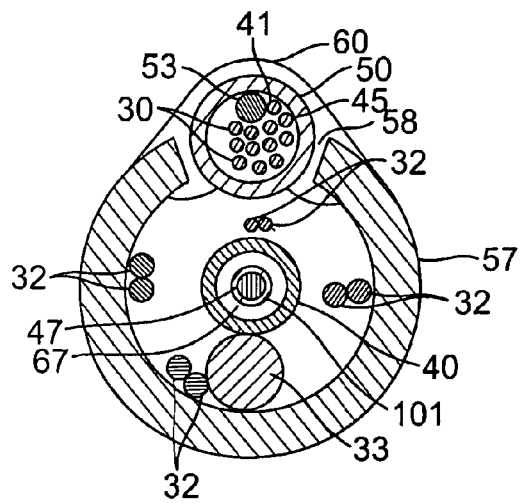
FIG. 6c is an end cross-sectional view of a connector tubing of FIGS. 6a and 6b, taken along line c-c.

As shown in FIGS. 6*a*-6*c*, the electromagnetic position sensor 33 is housed in the nonconductive connector tubing 57 as other components pass distally through the tubing 57, including the tubing 40 containing the puller wire 47 for the distal electrode assembly 17 (both from the lumen 27 of the tubing 13), the lead wires 32 (from the lumen 24) for ring electrodes 64 mounted on the distal assembly 17. The cable 36 for the sensor 33 passes through the lumen 26 of the intermediate section 14.

Distal the proximal electrode assembly 15 is the distal electrode assembly 17. As shown in FIGS. 1*b*, 7*a*-7*c*, the basket-shaped electrode assembly 17 extends between two fasteners, for example, nitinol rings 65 and 66, that define the proximal and distal ends of the assembly 17. The distal assembly 17 comprises a plurality of spines or arms 70 mounted, preferably generally evenly-spaced, around the tubing 40 which defines the longitudinal axis of the distal assembly 17. The spines have a convex curvature where each spine bows radially outwardly from the tubing 40, such that the spines converge at their distal and proximal ends at the rings 65 and 66.

With reference to FIG. 5*a*, each spine 70 of the basket assembly 17 comprises a flexible wire 72 (with or without shape memory) with a non-conductive covering or tubing 71 on which one or more ring electrodes 64 are mounted. In a preferred embodiment, the flexible wires 72 each comprise a flat Nitinol wire and the non-conductive tubing 71 each comprise a biocompatible plastic, such as polyurethane or PEBAX. The length of the tubings 71 is shorter than the length of the wires so that there are exposed proximal and distal ends of the wires not covered by the tubings. Alternatively, the spines 70 can be designed without the internal flexible wire if a sufficiently rigid non-conductive material is used for the non-conductive covering to permit expansion of the electrode assembly, so long as the spine has an outer surface that is non-conductive over at least a part of its surface for mounting of the ring electrodes 64. As will be recognized by one skilled in the art, the number of spines 70 can vary as desired depending on the particular application, so that the assembly has at least two spines, preferably at least three spines, and as many as eight or more spines. The term "basket-shaped" as used herein in describing the electrode assembly 17 is not limited to the depicted configuration, but can include other designs, such as spherical or egg-shaped designs, that include a plurality of expandable arms connected, directly or indirectly, at their proximal and distal ends.

Figure 8A:
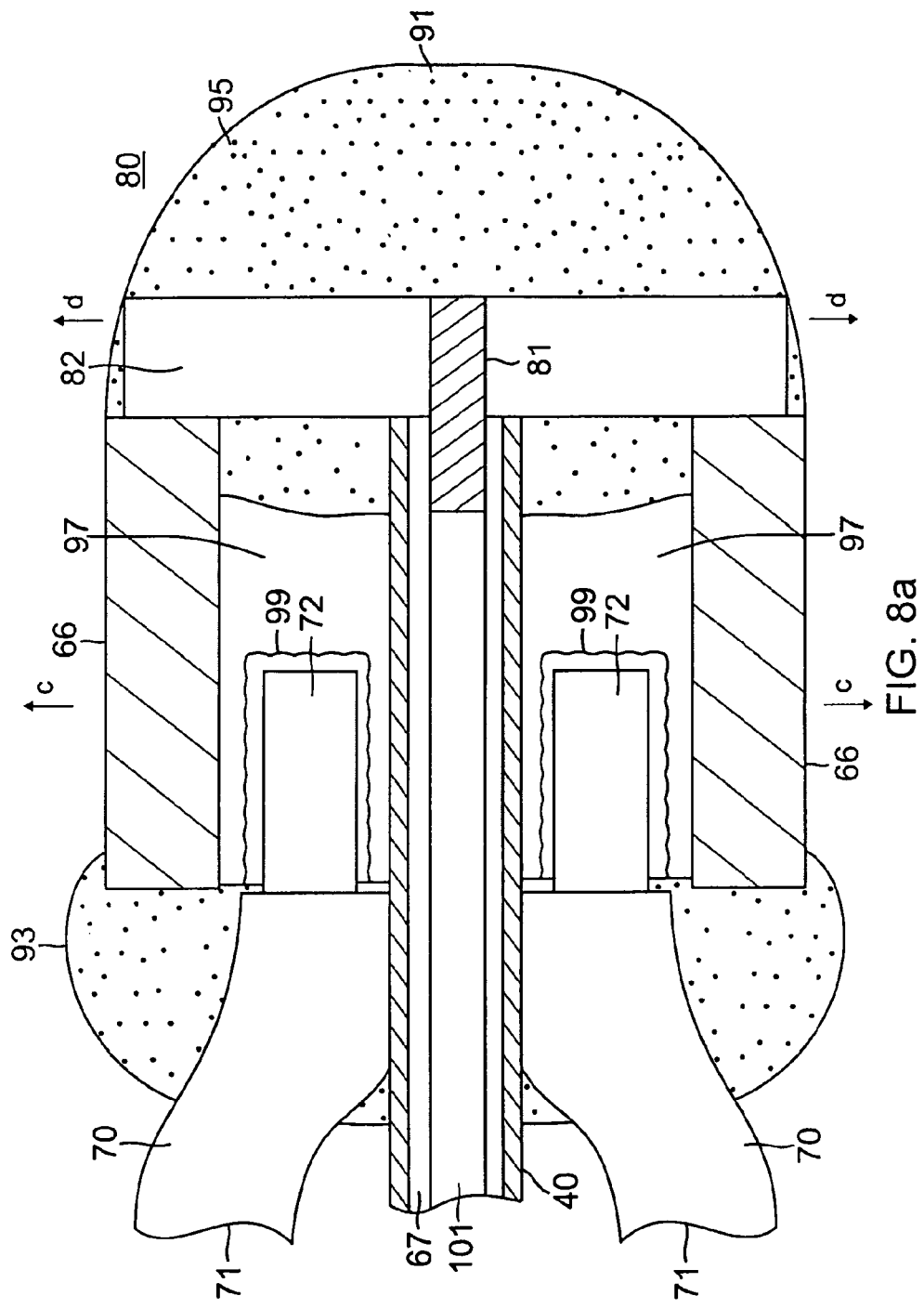
FIG. 8a is a side cross sectional view of an embodiment a catheter of the present invention, including a distal end of a distal electrode assembly, taken along one diameter.
Figure 8B:
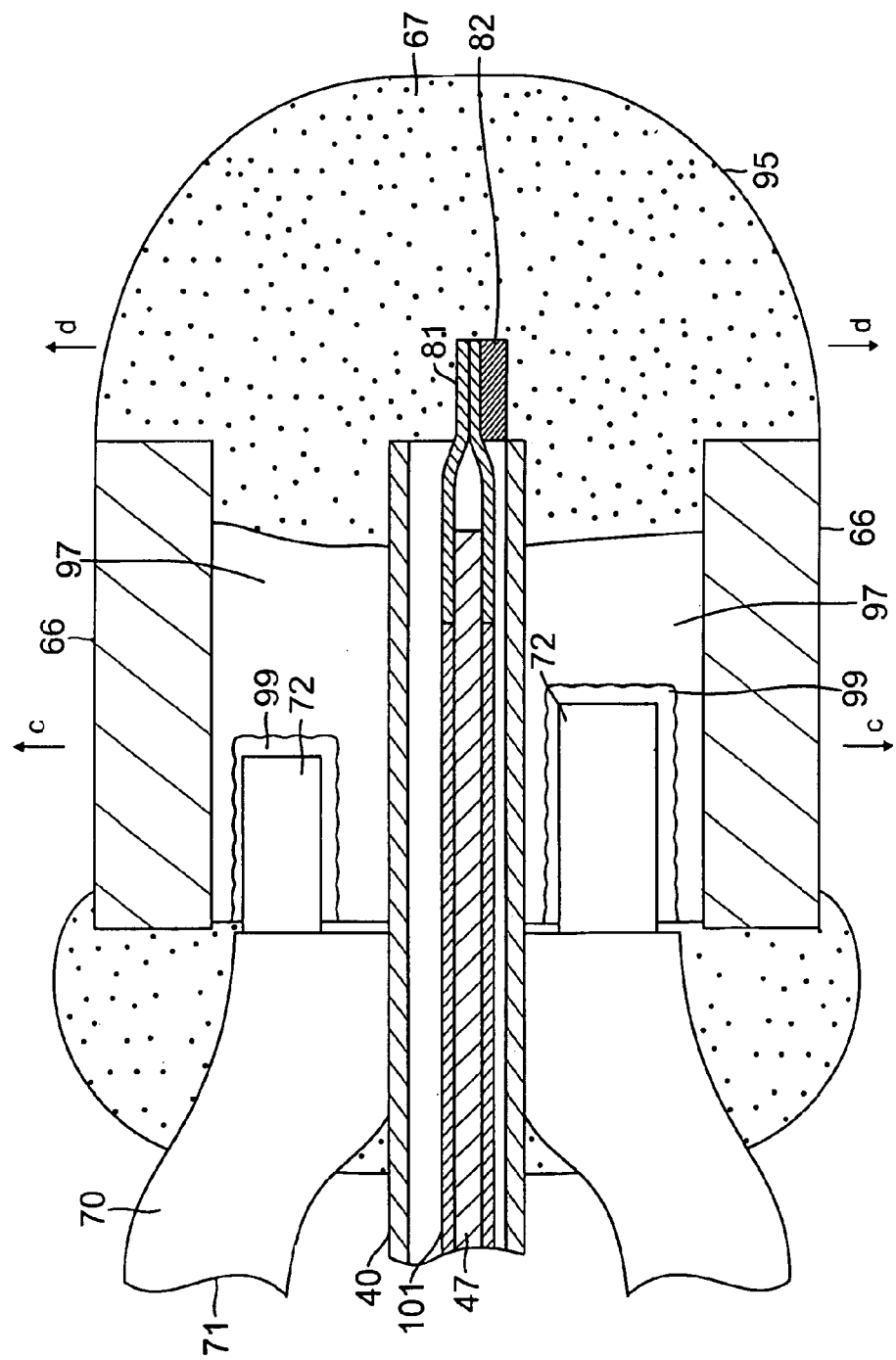
FIG. 8b is a side cross sectional view of an embodiment of a catheter of the present invention, including a distal end of a distal electrode assembly, taken along another diameter.
Figure 8C:
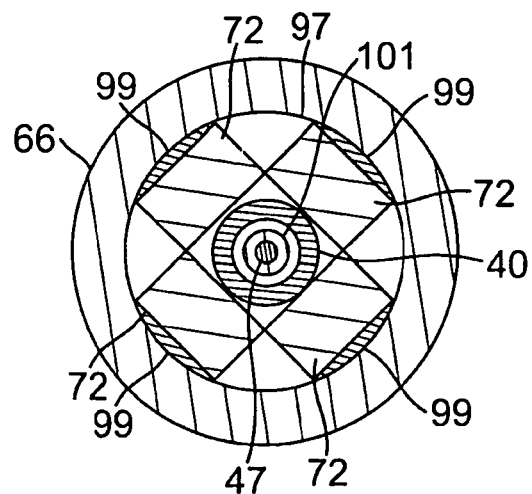
FIG. 8c is an end cross-sectional view of a distal end of a distal electrode assembly of FIGS. 8a and 8b, taken along line c-c.
Figure 8D:
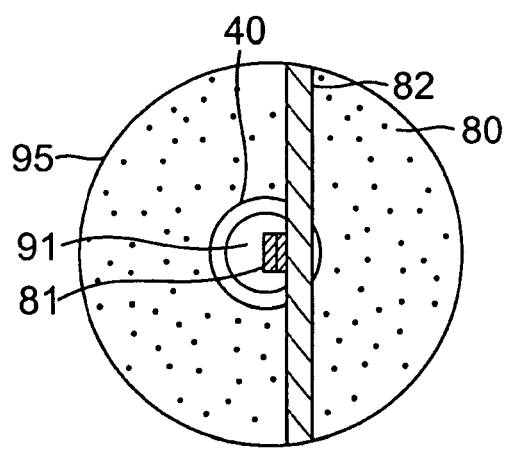
FIG. 8d is an end cross-sectional view of a distal dome tip of FIGS. 8a and 8b, taken along line d-d.

An embodiment of the distal end of the electrode assembly 17 is depicted in FIGS. 8*a* 8*c*. The distal end of a distal ring 66 is sealed by a biocompatible material, such as polyurethane, which is formed into an atraumatic dome 95. The exposed distal ends of the support members 72 of the spines 70 extending pass the coverings 71 are affixed, e.g., by soldering 99, preferably evenly-spaced, to an inner surface 97 of the ring 66. This junction between the spines 70, the tubing 40 and the proximal end of the ring 66 is sealed by a biocompatible material 93, such as polyurethane.

Figure 7A:
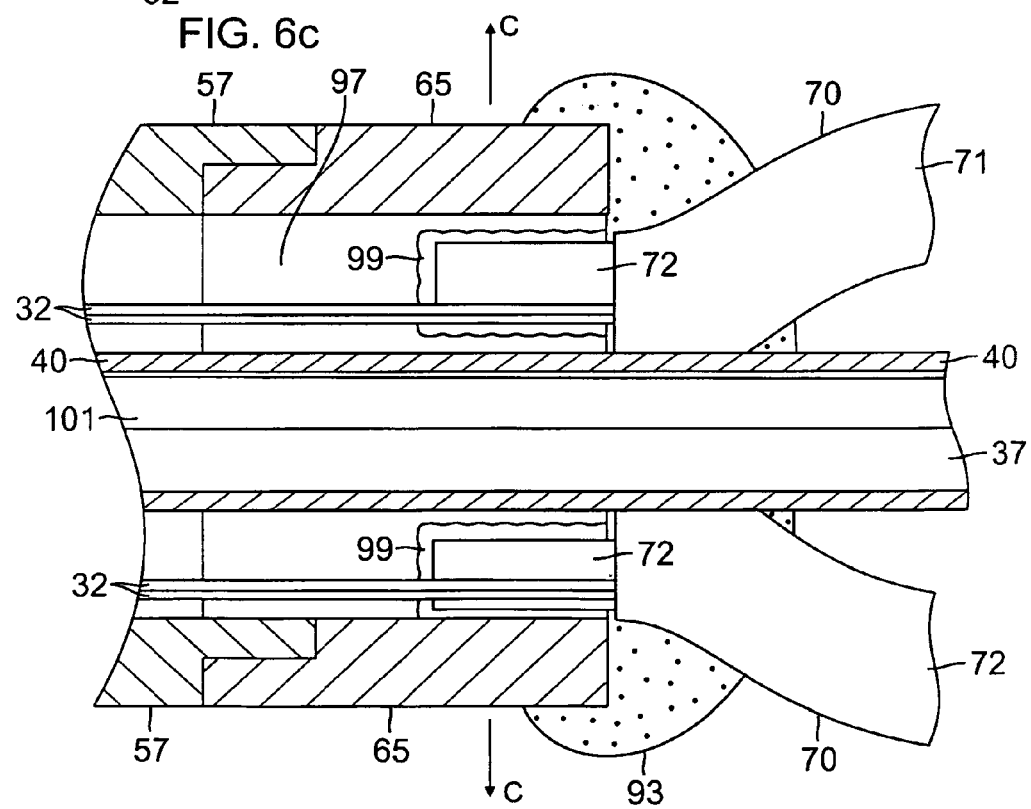
FIG. 7a is a side cross sectional view of an embodiment of a catheter of the present invention, including a proximal end of a distal electrode assembly, taken along one diameter.

An embodiment of the proximal end of the electrode assembly 17 has a similar construction, as shown in FIGS. 7*a*-7*c*, where the exposed proximal ends of the support members 72 are affixed to an inner surface 97 of the ring 65, e.g., by soldering 99 or glue, and the junction between the spines 70, the tubing 40 and the distal end of the ring 65 is sealed by a biocompatible material 93. The rings 65 and 66 can be made of metal or plastic, so long as it is sufficient rigid to achieve the above-stated function. It is understood that the spines can be formed from a unitary structure, such as a cylinder or tube that is laser cut with longitudinal cuts extending between its two opposing ends to form the spines. As would be recognized by one skilled in the art, other arrangements for attaching and arranging the spines and tubing 40 could also be used in accordance with the invention.

The tubing 40 is generally coaxial with the intermediate section 14. The tubing 40 has a distal end distal the distal ring 66 and a proximal end that is in the control handle 16 such that its lumen 67 provides a pathway for the second puller wire 47 between the control handle 16 and the distal assembly 17, as well as a pathway for a guidewire to extend through the entire length of the catheter for introduction of the catheter into a patient's body. Accordingly, the tubing 40 extends proximally through the rings 66 and 65, the connector tubing 57, the lumen 27 of the intermediate section 14, the central lumen of the catheter body 12, and the control handle 16.

The puller wire 47 for expanding the distal basket assembly 17 can made of any suitable metal, such as stainless steel or Nitinol, and is preferably coated with Teflon® or the like. The coating imparts lubricity to the puller wire. The puller wire preferably has a diameter ranging from about 0.006 to about 0.010 inch. The puller wire 47 is anchored at its proximal end in the control handle 16 and extends distally through the central lumen 18 of the catheter shaft 12 and the fourth lumen 27 of the intermediate section 14.

The distal end of the puller wire 47 is anchored in a distal tip 80 at the distal ring 66 by means of a T-shaped anchor 81 with a short stainless steel tubing crimped onto the puller wire 47, and a welded cross-piece 82 that is distal of the distal ring 66 and extends the width of the ring 66. So anchored against the ring 66, the puller wire 47 can be manipulated via the control handle 16 as described further below, thereby changing the curvature of the spines 70. In particular, as the puller wire is drawn proximally, the tubing 40 between the rings 65 and 65 is compressed thereby decreasing the separation between the rings 65 and 66, thus expanding (widening) the basket assembly 17 as the spines 70 bow further outwardly under the compression force applied by the puller wire 47. As shown in FIG. 1b, the basket-shaped assembly 17 can be varied between (and to adopt either of) a more elongated or resting configuration with a smaller diameter (broken lines) and an expanded configuration with a greater diameter (solid lines). The largest diameter at a mid-section of the basket assembly 17 can range between about 10 mm and 30 mm, and preferably between about 15 mm and 25 mm.

Each of the ring electrodes 52 and 64 of the electrode assemblies 15 and 17 is electrically connected to an appropriate mapping or monitoring system and/or source of ablation energy by means of respective electrode lead wires 30 and 32. Each electrode lead wire has its proximal end terminating in a connector 111 (FIG. 1) at the proximal end of the control handle 16. Distally, the electrode lead wires extend through the control handle 16, the central lumen 18 in the catheter body 12, and through the lumen 24 of the intermediate section 14. The portion of the lead wires 30 and 32 extending through the central lumen 18 of the catheter body 12, control handle 16 and proximal end of the lumen 24 are enclosed within a protective sheath (not shown), which can be made of any suitable material, preferably polyimide. The protective sheath can be anchored at its distal end to the proximal end of the intermediate section 14 by gluing it in the lumen 24 with polyurethane glue or the like.

Near the distal end of the intermediate section 14, the lead wires 30 for the lasso electrode assembly 15 and the lead wires 32 for the basket electrode assembly 17 diverge with the lead wires 30 entering the tubing 50 of the electrode assembly 15. The lead wires 32 for the basket electrode assembly 17 however extend out of the lumen 24, through the connector tubing 57, through the proximal ring 65 and through their respective covering 71 of the spines 71 of the assembly 17. Each lead wire is attached to its corresponding ring electrode by any suitable method.

A preferred method for attaching a lead wire to a ring electrode involves first making a small hole through the wall of the non-conductive covering. Such a hole can be created, for example, by inserting a needle through the non-conductive covering and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue 91 or the like (FIG. 5b). Alternatively, each ring electrode is formed by wrapping a lead wire around the non-conductive covering a number of times and stripping the lead wire of its own insulated coating on its outwardly facing surfaces.

The ring electrodes can be made of any suitable solid conductive material, such as platinum or gold, preferably a combination of platinum and iridium, and mounted onto the tubing with glue or the like. Alternatively, the ring electrodes can be formed by coating the tubing with an electrically conducting material, like platinum, gold and/or iridium. The coating can be applied using sputtering, ion beam deposition or an equivalent technique. While unipolar ring electrodes are illustrated herein, it is understood that bi-polar ring electrodes may be used.

The number of the ring electrodes on the assemblies can vary as desired. Preferably, the number of ring electrodes on the lasso assembly 15 ranges from about six to about twenty, preferably from about eight to about twelve, evenly spaced from each other. For the basket assembly 17, the number of ring electrodes on each spine ranges from about one to about four, preferably about three that are more concentrated in the outermost region of each spine. In a disclosed embodiment, a distance of approximately 5 mm is provided between each ring electrodes on the lasso assembly 15 and a distance of approximately 2 mm is provided between each ring electrode on each spine of the basket assembly.

Where any of the ring electrodes of the assemblies 15 and 17 are adapted for ablation, a pair of thermocouple wires can be provided to detect temperature of a respective ring electrode. In the disclosed embodiment, one pair of thermocouple wires 41 and 45 are provided, for example, for one of the ring electrodes of the proximal electrode assembly 15. The thermocouple wires 41 and 45 extend through the central lumen 18 of the catheter body 12 (FIG. 3A), through the lumen 26 of the tubing 13 of the intermediate section 14 (FIG. 4a), and through the tubing 50 of the proximal electrode assembly 15, where their distal ends are positioned near the ring electrode to sense temperature (FIG. 6a).

The deflection wire 34 for deflection of the intermediate shaft 14 has many similarities to the basket assembly puller wire 47 as described above. Some of the differences are described below.

The deflection wire 34 is anchored at its proximal end in the control handle 16 and extends distally through the central lumen 18 of the catheter shaft 12 and the second lumen 25 of the intermediate section 14 (FIG. 4a) where its distal end is anchored to the distal end of the intermediate section 14, as shown in FIG. 6b. Specifically, a T-shaped anchor is formed, which comprises a short piece of tubular stainless steel 43, e.g., hypodermic stock, which is fitted over the distal end of the deflection wire crimped to fixedly secure it to the puller wire. The distal end of the tubular stainless steel 43 is fixedly attached, e.g., by welding, to a cross-piece 44 formed of stainless steel ribbon or the like. The cross-piece 44 extends through a hole 46 formed in the tubing 13 and because the cross-piece 44 is larger than the hole 46 and, therefore, cannot be pulled through the hole, the cross-piece 44 anchors the distal end of the deflection wire 34 to the distal end of the intermediate section 14.

A compression coil 35 is situated within the catheter body 12 in surrounding relation to the deflection wire 34. In the disclosed embodiment, the compression coil 35 extends from the proximal end of the catheter body 12 to the proximal end of the intermediate section 14 (see FIG. 3b). The compression coil 35 is made of any suitable metal, preferably stainless steel, and is tightly wound on itself to provide flexibility, i.e., bending, but to resist compression. The inner diameter of the compression coil is preferably slightly larger than the diameter of the deflection wire 34. The Teflon® coating on the deflection wire 34 allows it to slide freely within the compression coil. Within the catheter body 12, the outer surface of the compression coil 35 is also covered by a flexible, non-conductive sheath 68, e.g., made of polyimide tubing. The compression coil is anchored at its proximal end to the outer wall 20 of the catheter body 12 by a proximal glue joint and to the intermediate shaft 14 by a distal glue joint. Within the lumen 25 of the intermediate shaft 14, the deflection wire 34 extends through a plastic, preferably Teflon®, puller wire sheath 37, which prevents the deflection wire 34 from cutting into the wall of the tubing 13 when the intermediate section 14 is deflected.

A compression coil 103 is also provided for the puller wire 47 extending through the tubing 40. In the disclosed embodiment, the distal end of the coil 103 is in the connector tubing 57, a few millimeters distal of the location of the opening 58.

The proximal end of the compression coil 103 is at or near the proximal end of the catheter body 12. A tubing 101 surrounds the puller wire 47 within the compression coil 103. The tubing 101 may be a tight fitting tubing of TEFLON.

Figure 9:
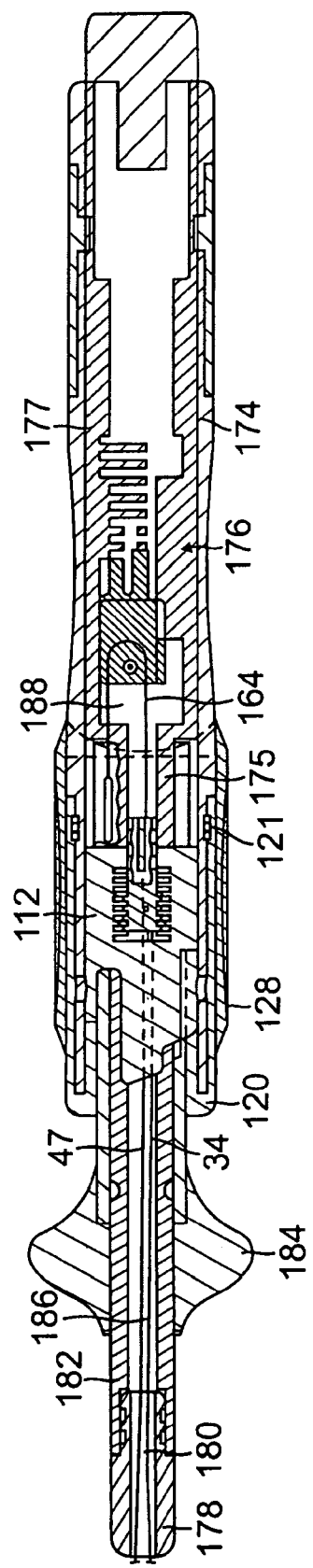
FIG. 9 is a side cross sectional view of an embodiment of a control handle of the present invention.

Separate and independent longitudinal movement of the deflection wire 34 and the puller wire 47 relative to the catheter body 12, which results in, respectively, deflection of the intermediate section 14 and expansion of the distal electrode assembly 17, is accomplished by suitable manipulation of the control handle 16. A suitable control handle is disclosed in U.S. Pat. No. 6,987,995 to Drysen entitled Multifunctional Catheter Handle, the entire disclosure of which is hereby incorporated by reference. As shown in FIGS. 1 and 9, the control handle 16 has a thumb control knob 184, and a cam 120 rotatable by means of a flexible grip 128 that can be independently manipulated by a user.

Figure 10:
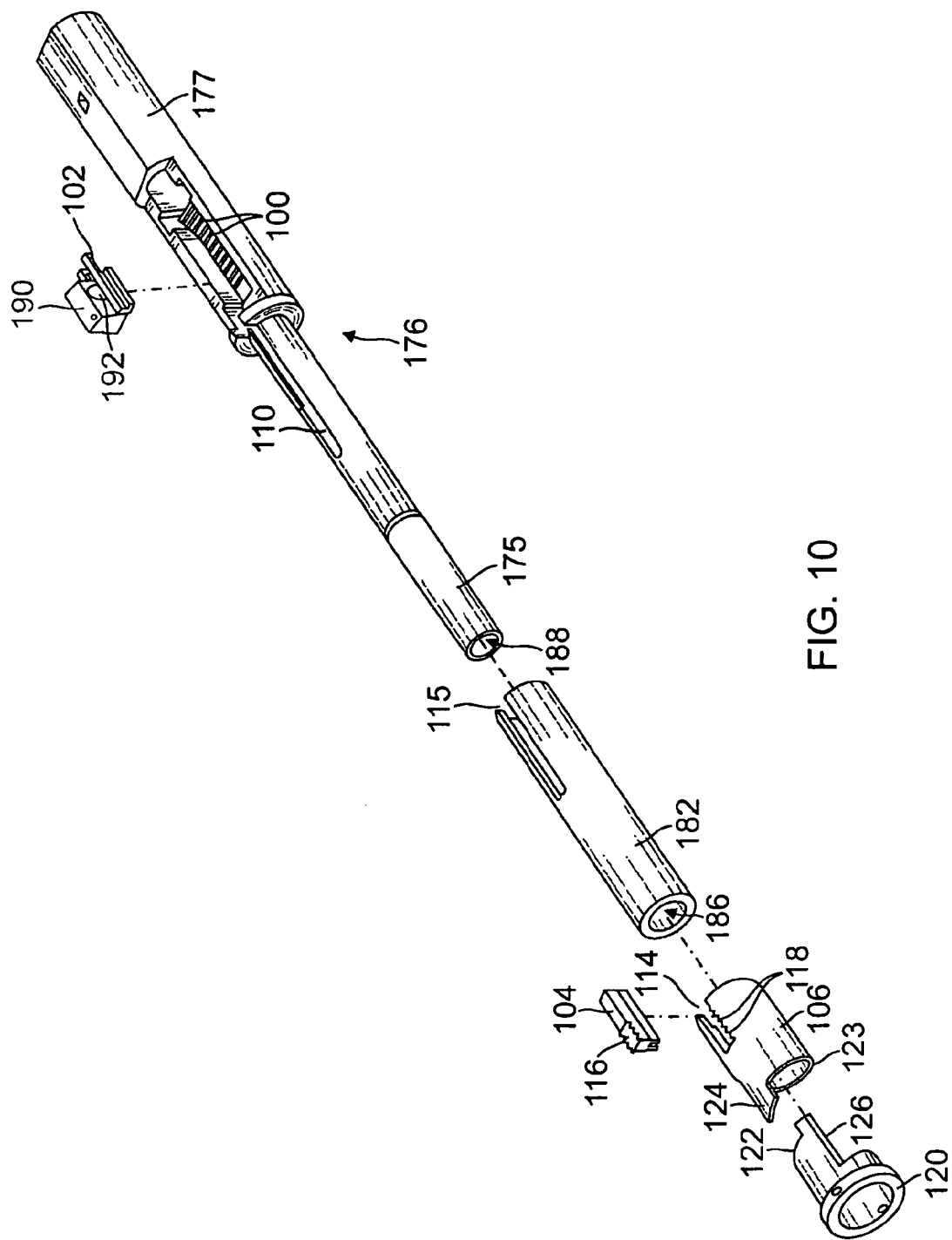
FIG. 10 is an exploded perspective view of interior components of the control handle shown in FIG. 9.
Figure 11:
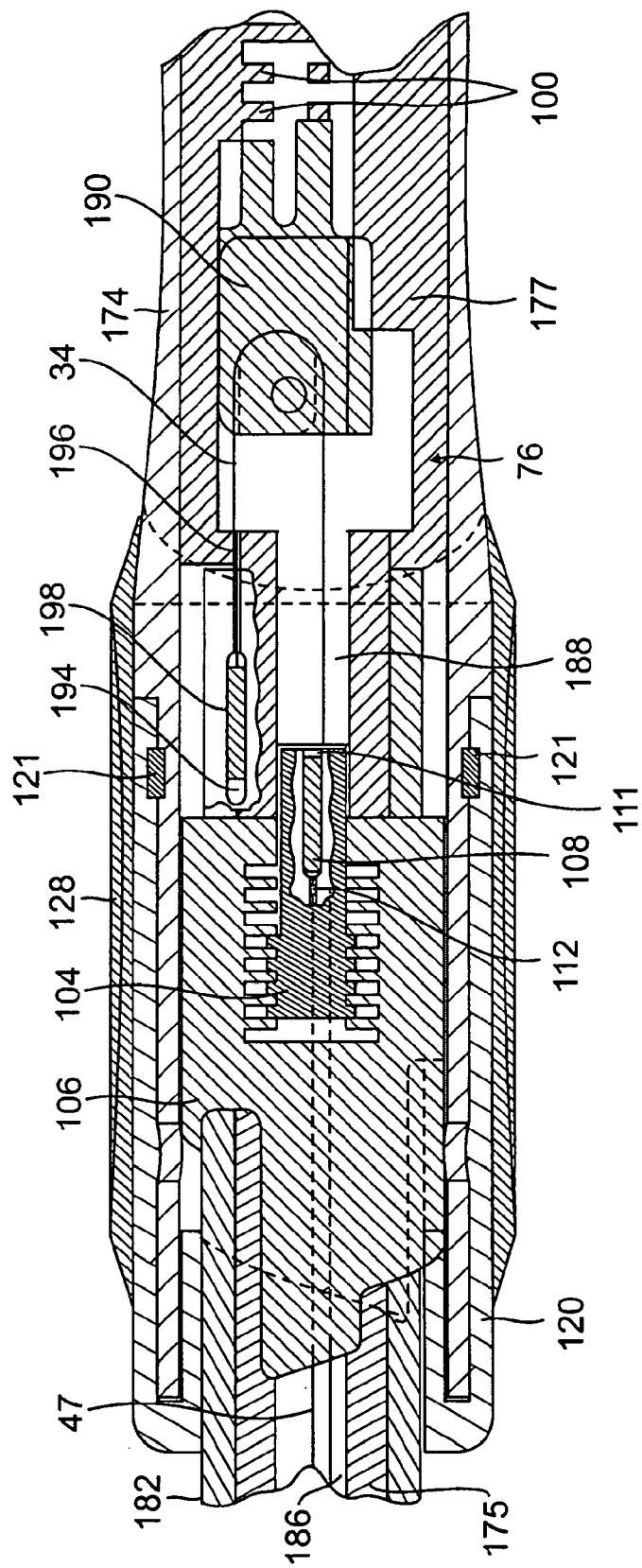
FIG. 11 is an enlarged side cross-sectional view of the control handle of FIG. 9 showing a deflection wire adjuster and a contraction wire adjuster.

In the embodiment of FIGS. 9 to 11, the control handle 16 includes a handle body 174 in which a core 176 is fixedly mounted. Although in the depicted embodiment, the core 176 is separate from the handle body 174, the core could instead be formed as a single unitary piece with the handle body. The core has a generally cylindrical distal region 175 and a generally cylindrical proximal region 177 having a larger diameter than the distal region. For longitudinal movement of the deflection wire 34, a piston 182 is slidably mounted over the distal region 177 of the core 176. The proximal end of the piston 182 is maintained within the handle body 174, and the distal end of the piston extends outside the handle body. The thumb knob 184 is mounted in surrounding relation to a portion of the distal end of the piston 182 so that the user can more easily move the piston longitudinally relative to the core 176 and handle body 174. The proximal end of the catheter body 12 is fixedly mounted to the distal end of the piston 182 through a tip portion 178 that is mounted on the distal end of the piston. The proximal end of the catheter body 12 is inserted into an axial passage 180 in the tip portion and optionally glued in place. The piston includes an axial passage 186 in communication with the axial passage 180 of the tip portion 178, and the core 176 includes an axial passage 188 in communication with the axial passage in the piston.

The lead wires 30 and 32 (not shown for better clarity of other components in the control handle), the puller wire 47 and deflection wire 34 that extend through the catheter body 12 extend out the proximal end of the catheter body and through the axial passages in the tip portion 178, piston 182 and core 176. The lead wires can extend out the proximal end of the control handle 16 or can be connected to a connector (not shown) that is incorporated into the control handle, as is generally known in the art.

The proximal end of the deflection wire 34 is anchored to the core 176. As best seen in FIG. 11, the portion of the axial passage 188 extending through the proximal region 177 of the core 176 has a larger diameter than the portion of the axial passage extending through the distal region 175 of the core 176. A deflection wire adjuster 190 is adjustably mounted, as described further below, in a portion of the axial passage 188 near the distal end of the proximal region 177 of the core 176. The deflection wire adjuster 190 has an opening 192 extending therethrough in a direction generally transverse, and preferably generally perpendicular, to the axial passage 188 of the core 176. The deflection wire 34 extends through the opening 192 in the deflection wire adjuster 190 such that the deflection wire changes directions.

The distal region 177 of the core 176 includes a generally rectangular opening 194 that extends generally parallel to the axial passage 188 of the core. A channel 196 connects the proximal end of the generally rectangular opening 194 to the distal end of the portion of the axial passage 188 in the proximal region 175 of the core 176. The proximal end of the deflection wire 164 extends through the channel 196 and into the generally rectangular opening 194. A deflection wire anchor 198, which can comprise a short piece of hypodermic stock, is fixedly attached, for example, by crimping, to a portion of the proximal end of the deflection wire 164 within the generally rectangular opening 194. The deflection wire anchor 198 has a diameter greater than the width of the channel 196 and thus prevents the proximal end of the deflection wire 34 from being pulled through the channel, thereby anchoring the deflection wire to the core 176. Thus, the deflection wire anchor 198 is fixedly mounted to the core 176 even though the deflection wire anchor still has a small amount of free play within the opening 194.

In use, the piston 182 is moved distally relative to the handle body 74 and core 176 by means of the thumb knob 184, thereby pulling the catheter body 12 distally relative to the deflection wire 34, which is anchored to the core. As a result, the deflection wire 34 pulls on the side of the intermediate shaft 14 to which it is anchored, thereby deflecting the distal shaft in that direction. To straighten the intermediate shaft 14, the piston 182 is moved proximally back to its original position relative to the handle body 174 and core 176.

Manipulation of the deflection wire adjuster 190 adjusts the amount of free play in the deflection wire 34. As noted above, the deflection wire adjuster 190 is adjustably mounted in a portion of the axial passage 188 near the distal end of the proximal region 177 of the core 176. The portion of the axial passage 88 in which the deflection wire adjuster 190 is mounted includes a series of ridges 100 extending along the surface of the core 176, with the ridges being generally perpendicular to the axis of the core. The deflection wire adjuster 190 carries an outwardly extending tab 102 that fits in the spaces between the ridges 100. The deflection wire adjuster 190 can be moved along the length of the core 176 and snapped into place by placing the tab 102 between two ridges 100. As the deflection wire adjuster 190 is moved proximally (away from catheter body 12) less free play is provided for the deflection wire 34. The precise mechanism for adjusting the amount of free play of the deflection wire 34 is not critical, and alternative mechanisms can be provided. Alternatively, the deflection wire 34 can be anchored directly to the core 176 so that it is not adjustable.

The control handle 16 is also used for longitudinal movement of the puller wire 47 for expanding the basket assembly 17 by means of the flexible grip 128. The puller wire 47 extends from the catheter body 12, through the axial passage 186 in the piston 182 and through the axial passage 188 within the distal region 175 of the core 176. The proximal end of the puller wire 47 is anchored to a contraction wire adjuster 104 that is slidably mounted in the core 176.

The puller wire adjuster 104 is generally rectangular having a bottom region 108 that extends downward through a slot 110 in the proximal region 177 of the core 176, the slot being in communication with the axial passage 188 of the core. The proximal end of the puller wire 47, which, as noted above, extends through the axial passage 188, is anchored in the puller wire adjuster 104 in a manner very similar to the manner in which the deflection wire 164 is anchored to the core 176, as described above. Specifically, a puller wire anchor 108, which can comprise a short piece of hypodermic stock, is fixedly attached, for example, by crimping, to a portion of the proximal end of the puller wire 47 within an opening 110 in the puller wire adjuster 104. A channel 112 connects the opening 110 to the axial passage 88 in the core.

The puller wire anchor 98 has a diameter greater than the width of the channel 112 and thus prevents the proximal end of the puller wire 47 from being pulled through the channel, thereby anchoring the puller wire to the puller wire adjuster 104. The distal end of the puller wire adjuster 104 is adjustably attached to a cam receiver 106. The cam receiver 106 is generally tubular, having a short slot 114 extending from its proximal end sized to receive the distal end of the puller wire adjuster 104. The cam receiver 106 is slidably mounted over the piston 182 and the distal region 175 of the core 176 with the bottom portion of the puller wire adjuster 104 positioned in the slot 114 in the core and a corresponding slot 115 in the piston. Thus, the puller wire anchor 98 is fixedly mounted to the cam receiver 106 through the puller wire adjuster 104, even though the puller wire anchor has some free play within the opening 110 in the puller wire adjuster.

As shown in FIG. 10, the top of the distal end of the puller wire adjuster 104 includes a series of outwardly extending teeth 116 that mate with a plurality of notches 118 within the slot 114 of the cam receiver 106 so that the puller wire adjuster can be snapped into the cam receiver. The position of the puller wire adjuster 104 relative to the cam receiver 106 can be longitudinally adjusted by repositioning the teeth 116 relative to the notches 118, to thereby adjust the tension on the puller wire 47. Alternatively, the puller wire 40 is not adjustable, in which case the puller wire anchor 98 is mounted within an opening (not shown) within the cam receiver 106.

Longitudinal movement of the cam receiver 106 and puller wire adjuster 104 relative to the core 76, to which the catheter body 12 is indirectly mounted, results in longitudinal movement of the puller wire 47 relative to the catheter body. Longitudinal movement of the cam receiver 106 is accomplished through a cam 120 mounted in the control handle 16 in surrounding relation to the piston 182 and distal region 175 of the core 176. A retaining ring 121 maintains the longitudinal position of the cam 120 relative to the handle body 74.

The cam 120 includes a ramped proximal surface 122. The cam receiver 106 includes a ramped distal surface 123 and an outwardly extending tab 124 at the most distal point of the ramped distal surface. The tab 124 contacts the ramped proximal surface 122 of the cam 120. When the cam 120 is rotated counterclockwise, the ramped proximal surface 112 correspondingly rotates and pushes the cam receiver 104 proximally relative to the core 176 and catheter body 12. As the cam receiver 104 and the attached puller wire adjuster 104 are moved proximally relative to the core 176 and catheter body 12, the puller wire 47 is pulled proximally to thereby expand the basket assembly 17.

The ramped proximal surface 122 of the cam 120 includes an outwardly extending tab 126 at its most proximal point. As the cam 120 is rotated counterclockwise, the tab 124 on the cam receiver 104 contacts the tab 126 on the ramped proximal surface 122, thereby prohibiting further rotation of the cam relative to the cam receiver. As the cam 120 is rotated clockwise, the tab 126 on the ramped proximal surface 122 pushes the tab 124 on the cam receiver 104 such that the cam receiver moves distally, thereby releasing the tension on the puller wire 47 so that the basket assembly 17 returns to its original configuration. As would be recognized by one skilled in the art, the direction of the ramped proximal surface 122 can be changed so that clockwise rotation of the cam 120 causes expansion of the basket assembly and counterclockwise rotation causes it to return to its original configuration. The flexible grip 128 is provided over the cam 120 for the user to more easily and comfortably rotate the cam 120.

In use, a suitable guiding sheath is inserted into the patient with its distal end positioned at a desired tubular region of the heart such as a pulmonary vein. An example of a suitable guiding sheath for use in connection with the present invention is the Preface™ Braiding Guiding Sheath, commercially available from Biosense Webster, Inc. (Diamond Bar, Calif.). The distal end of the sheath is guided toward the ostium of the pulmonary vein and a catheter of the present invention is fed through the guiding sheath until its distal and proximal electrode assemblies 15 and 17 both extend out of the distal end of the guiding sheath. As the catheter is fed through the guiding sheath, the spines of the basket assembly 17 are pressed inwardly toward the tubing 40 so that the assembly 17 adopts a more elongated profile, and the lasso assembly 15 is straightened with the distal dome end 54 leading through the sheath. Once the distal tip 80 of the catheter is positioned at the desired treatment location, the guiding sheath is pulled proximally, exposing the deflectable intermediate section 14 and the assemblies 15 and 17 to extend outside the sheath, whereupon the assemblies return to their original shapes due to the shape-memory of the support members 53 and 72. The user can manipulate the thumb control 184 of the control handle 16 to deflect the intermediate section 14 for positioning the assemblies 15 and 17 as appropriate. With proper manipulation, the basket assembly 17 is inserted into a pulmonary vein or other tubular region (such as the coronary sinus, superior vena cava, or inferior vena cava) so that the lasso assembly 15 comes into contact and sits on the ostium and the electrodes 52 are positioned circumferentially about the ostium. Manipulation of the flexible grip 128 of the control handle 16 expands the basket assembly 17 within the tubular region so that the electrodes 64 come into contact with a circumferential inner surface of the tubular region. The user may then apply energy (e.g., RF, laser, or microwave) to the electrodes 52 of the lasso assembly 15 to form a generally circumferential lesion ring around the ostium, especially by rotating the catheter handle 16 and the catheter body 12 which rotation translates along the length of the catheter to the electrode assemblies 15 and 17. The electrodes 64 of the basket assembly 17 are in contact with a circumference inside the tubular region. Preferably at least about 50%, more preferably at least about 70%, and still more preferably at least about 80% of the circumference of the generally circular main region is in contact with a circumference inside the tubular region. The circular arrangement of the electrodes 64 of the distal basket assembly 15 permits measurement of the electrical activity at that circumference of the tubular structure so that the catheter can provide real-time and continuous feedback of the potential recordings or electrograms (ECGs) inside the tubular region as a circumferential ablation is performed around the vein's ostium by the proximal lasso assembly 15.

In an alternative embodiment, the deflection wire 34 is replaced by or adapted to function as a contraction wire to contract the generally circular main region 39 to thereby reduce its diameter. The foregoing description of the deflection wire as to its configuration in the control handle 16, the catheter shaft 12 and the intermediate section 14 applies to this alternative embodiment, except for differences that include the extension of the wire through the tubing 50 of the lasso assembly 15 and its distal end being anchored in the distal tip 54. Contraction of the lasso assembly could still be accomplished by manipulation of the thumb control knob 184 as described above.

As understood by one of ordinary skill in the art, the tubing 50 may be adapted, such as a plastic tube of multiple layering, including an inner layer of polyimide over which a braided layer is formed, the braided layer comprising a braided stainless steel mesh or the like, as is generally known in the art, for reducing the tendency for contraction wire to straighten the preformed curve of the lasso assembly 15. A thin plastic layer of polytetrafluoroethylene is provided over the braided layer to protect the braided layer from getting tangled with the lead wires within the non-conductive cover. The plastic tube has a proximal end anchored to the distal end of the intermediate section 14. The support member 53 extends through the plastic tube with the contraction wire. The distal end of the support member 53 and the contraction wire are soldered or otherwise attached to a small stainless steel tube 44. With this arrangement, the relative positions of the contraction wire and the support member 53 can be controlled so that the contraction wire can be positioned on the side of the generally circular region closer to the center of the generally circular region, as described above. The contraction wire on the inside of the curve pulls the support member 53 to the inside of the curve, enhancing contraction of the generally circular region 39. Further, when the plastic tube 42 includes a braided layer, it keeps the contraction wire from tearing through the non-conductive cover.

It is understood by one of ordinary skill in the art that the catheter of the present invention can be readily adapted so that either thumb control or the flexible grip of the control handle 16 can deflect the intermediate section 14, contract the lasso assembly 15 or expand the basket assembly 17 by means of a tensile member, such as a deflection wire, a contraction wire, or puller wire. It is further understood that the electrode assemblies 15 and 17 can each be adapted with sensing ring electrodes, ablation ring electrodes or combinations thereof as desired or appropriate.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter comprising: an elongated catheter body generally defining a catheter axis; a distal electrode assembly mounted on a distal end of the catheter body, the distal electrode assembly having a first elongated member defining a longitudinal axis and a plurality of spines surrounding the first elongated member and converging at their proximal and distal ends, the proximal end of the spines are anchored to the distal end of the catheter body, each spine comprising at least one electrode and having a curvature so that the spine bows radially outwardly from the first elongated member; a proximal electrode assembly mounted on the distal end of the catheter body proximal of the distal electrode assembly and having a second elongated member configured with a generally radial portion and a generally circular portion generally transverse to the catheter axis, the generally circular portion comprising a plurality of electrodes; a control handle at a proximal end of the catheter body; a first tensile member extending between the control handle and the distal electrode assembly; and a second tensile member extending between the control handle and the proximal electrode assembly, wherein the control handle is configured for user manipulation of the first tensile member to change the curvature of the spines of the distal electrode assembly, and for user manipulation of the second tensile member to contract the proximal electrode assembly.

2. The catheter of claim 1, wherein the electrodes on the distal electrode assembly are adapted for sensing electrical activity in the heart and the electrodes on the proximal electrode assembly are adapted for ablation.

3. The catheter of claim 1, wherein the spines have shape-memory.

4. The catheter of claim 1, wherein the second elongated member of the proximal electrode assembly has shape-memory.

5. The catheter of claim 1, wherein the distal electrode assembly is adapted to contact an inner circumferential surface of a tubular region of the heart and the proximal electrode assembly is adapted to contact an opening of the tubular region.

6. The catheter of claim 1, wherein the distal electrode assembly is adapted to contact an inner circumferential surface of a pulmonary vein and the proximal electrode assembly is adapted to contact an ostium of the pulmonary vein.

7. The catheter of claim 1, wherein the control handle comprises:
a handle body;
a core mounted within the handle body, the core having a longitudinal passage extending therethrough;
a piston having a proximal end mounted in the handle body and a distal end extending outside the handle body, the piston being longitudinally moveable relative to the core and handle body;
a first anchor fixedly mounted to the core;
a cam receiver mounted within the handle body so that the cam receiver is longitudinally slidable relative to the piston and core;
a second anchor fixedly mounted to the cam receiver; and
a generally cylindrical cam mounted distal to the cam receiver in surrounding relation to the piston, wherein rotation of the cam relative to the piston causes longitudinal movement of the cam receiver and second anchor,
wherein a proximal end of the first tensile member is connected to one of said first and second anchors for direct or indirect manipulation by a user of one of the piston and the cam receiver to change the curvature of the spines.

8. The catheter of claim 7, wherein the one anchor is adapted to draw the first tensile member proximally to increase the curvature of the spines.

9. The catheter of claim 7, further comprising:
an intermediate section between the catheter body and the proximal electrode assembly,
wherein a proximal end of the second tensile member is connected to the other anchor for user manipulation of the other anchor for contracting the proximal electrode assembly.

10. The catheter of claim 9, wherein a distal end of the second tensile member is anchored at or near a distal end of the proximal electrode assembly.

11. The catheter of claim 1, wherein the first elongated member of the distal electrode assembly is a tube through which a distal portion of the first tensile member extends.

12. The catheter of claim 1, wherein each spine has a non-conductive outer surface on which one or more ring electrodes are mounted.

13. The catheter of claim 9, wherein each spine has a support member.

14. The catheter of claim 13, wherein the support member is a nitinol wire.

15. The catheter of claim 1, wherein the distal electrode assembly comprises at least three spines.

16. The catheter of claim 1, wherein the distal electrode assembly comprises at least five spines.

17. The catheter of claim 8, wherein the proximal end of the first tensile member is fixedly attached, directly or indirectly, to the first anchor so that longitudinal movement of the piston relative to the handle housing results in longitudinal movement of the first tensile member relative to the catheter body to thereby expand the distal electrode assembly.

\* \* \* \* \*